(12) United States Patent
Buisson et al.

(10) Patent No.: US 7,402,192 B2
(45) Date of Patent: Jul. 22, 2008

(54) METHOD AND DEVICE FOR CONTINUOUSLY TREATING WASTE WATER OF INDUSTRIAL ORIGIN BY WATER VAPOUR STRIPPING

(75) Inventors: Jean-François Buisson, Martigues (FR); Frédéric Pouly, Lyons (FR)

(73) Assignee: Total Fina Elf France, Puteaux (FR)

( * ) Notice: Subject to any disclaimer, the term of this patent is extended or adjusted under 35 U.S.C. 154(b) by 386 days.

(21) Appl. No.: 10/433,332

(22) PCT Filed: Nov. 30, 2001

(86) PCT No.: PCT/FR01/03792

§ 371 (c)(1),
(2), (4) Date: Nov. 26, 2003

(87) PCT Pub. No.: WO02/43829

PCT Pub. Date: Jun. 6, 2002

(65) Prior Publication Data

US 2004/0083885 A1    May 6, 2004

(30) Foreign Application Priority Data

Dec. 1, 2000    (FR) .................................. 00 15568

(51) Int. Cl.
*B01D 19/00*    (2006.01)
(52) U.S. Cl. ................... 95/8; 95/9; 95/263; 96/156; 96/202
(58) Field of Classification Search ................. 95/8, 95/9, 263; 196/98; 250/281; 96/156, 202; 364/501, 578, 151; 422/82.05
See application file for complete search history.

(56) References Cited

U.S. PATENT DOCUMENTS

| | | | | | |
|---|---|---|---|---|---|
| 2,553,469 | A | * | 5/1951 | Pellettere | 62/628 |
| 2,881,235 | A | * | 4/1959 | Pool | 585/701 |
| 2,977,289 | A | * | 3/1961 | Kron | 203/3 |
| 3,282,799 | A | * | 11/1966 | MacMullan | 203/2 |
| 3,697,384 | A | * | 10/1972 | Walker | 203/1 |
| 3,824,185 | A | * | 7/1974 | Caldwell et al. | 210/603 |
| 3,840,437 | A | | 10/1974 | Awan et al. | |

(Continued)

FOREIGN PATENT DOCUMENTS

| | | | |
|---|---|---|---|
| FR | 1 398 730 A | | 9/1965 |
| GB | WO 00/00261 | * | 1/2000 |
| WO | WO 97/35191 | * | 9/1997 |

OTHER PUBLICATIONS

"Unit Operation of Chemical Engineering", McCable et al, 6th Edition 1982, Chapter 22.*

*Primary Examiner*—Duane Smith
*Assistant Examiner*—Ives Wu
(74) *Attorney, Agent, or Firm*—Sughrue Mion, PLLC

(57) ABSTRACT

The invention concerns a method characterised in that it consists in: determining online at least an ultraviolet spectrum portion of at least one of the compounds present in one or the other of the waste water feeding circuits (7, 13) or of the column (8) waste water output (16); qualitatively and quantitatively determining, by mathematical processing of the measured intensity levels, at least a contaminant present in the samples; on the basis of the results obtained and by comparing with pre-defined setpoint values, in restoring said data in the form of electric signals, which control the waste water supply and the stripping column water vapour flow rates.

18 Claims, 2 Drawing Sheets

U.S. PATENT DOCUMENTS

| | | |
|---|---|---|
| 4,113,615 A | 9/1978 | Gorbaty |
| 4,358,822 A * | 11/1982 | Sanchez ..................... 700/31 |
| 4,444,571 A * | 4/1984 | Matson .......................... 95/48 |
| 4,759,944 A | 7/1988 | Fasi et al. |
| 5,343,407 A * | 8/1994 | Beauford et al. ............ 700/270 |
| 6,395,228 B1 * | 5/2002 | Maggard et al. ......... 422/82.05 |

* cited by examiner

METHOD AND DEVICE FOR CONTINUOUSLY TREATING WASTE WATER OF INDUSTRIAL ORIGIN BY WATER VAPOUR STRIPPING

This disclosure is based upon, and claims priority from, French patent application No. 15568 filed Dec. 1, 2000, the contents of which are incorporated by reference herein.

The present invention concerns a method and device for continuous processing by water vapor stripping of industrial wastewater that may contain contaminants, that is, by extraction of the most volatile parts contained in said water.

It is known that in all large industrialized countries, the laws impose standards that are stricter and stricter and more limiting concerning the quality of wastewaters produced by various industrial facilities, which are disposed of into the, natural environment. Indeed, said waters may have been contaminated by various pollutants that are hazardous to humans and the environment when they are used, and it is therefore necessary and essential to give them appropriate processing before returning them to the natural environment.

Thus, in oil refineries, which constitute a type of industrial facility that will be referred to more specifically in the following description, without however being limited thereto, the waters called "process waters," originating from the different units of the refinery, represent the majority of waters that must undergo processing before they are reintegrated into their initial environment. Indeed, before running these waters through various physical and biological finish actions, they are first given a primary application called stripping which makes it possible to extract the most volatile parts they contain by physical action. It is for this purpose that an oil refinery is usually equipped with at least one stripping device, called "stripper" in the industry, in which the wastewaters produced by the different processes are given a counter-current treatment by a flow of water vapor in a column housing several horizontal plates.

The process waters treated in this way, which contain only limited quantities of a number of pollutants such as ammonium hydroxide, sulfides, or various phenols, are evacuated to the lower part of the stripper, then mixed with runoff water, and are finally given various treatments called finishing, before being discarded into the natural environment.

Among these treatments are:
  a pretreatment by decantation with surface skimming to eliminate droplets of insoluble hydrocarbons and the largest particles of suspended particulate matter (SPM);
  a physical-chemical treatment of flocculation and filtration to eliminate most of the residual insoluble hydrocarbons, the small suspended particulate matter and metals that are dissolved or in suspension;
  a filtration treatment, such as a trickling filter, in particular to reduce the organic load (total organic carbon, or TOC), the concentration in phenols and the concentration in dissolved hydrocarbons;
  a final clarification treatment.

In a refinery, the stripper placed upstream of these additional treatments therefore has an essential function, because it receives nearly all of the waters produced by various sources (desalting of crude oils, distillation units, gasoils desulfurization unit, cat crackers, etc.), heavily contaminated by, among other things, gases as well as toxic and malodorous compounds.

A stripper is generally composed of a column inside which plates are arranged at several levels and in which the waters to be processed are introduced at the column head and the water vapor at the bottom. Currently on the market there are several variations of strippers, particularly those:
  without column head condenser (the simplest);
  with head condenser and control of the reflux rate;
  with head condenser and bottom reboiler, thus replacing the injection of the water vapor flows;
  with two superimposed columns for better efficiency of stripping of heavily contaminated waters.

In order to limit and protect the additional treatments of waters exiting the stripper, and consequently to prevent or limit, for example, the deterioration of the bio-filter used in one of these treatments, as well as to obtain maximum stripping effectiveness, it is therefore essential and even indispensable that the stripper work under the best operating conditions.

In order to optimize this operation, the operator can deal with the following parameters:
  the feed flow rate of stripping vapor,
  the feed flow rate of wastewater to be treated, and, for certain stripper technologies:
  the reflux rate of the water at the column head,
  the reboil rate at the column bottom.

Each type of stripper is selected in accordance with the specificities of the industrial sites and the treatments to be performed, according to the standards in force for wastewaters, which may have a greater or lesser load of contaminants.

Because the adjustment of these parameters is directly related to the nature and concentrations of the contaminants present in the process waters, the refiner must be able to have such information at all times in order to optimize the operation of the stripper. At present, however, there is no satisfactory method for the instantaneous or quasi-instantaneous analysis of the composition of contaminants and the degree of pollution of the wastewaters arriving at the stripper. The only methods of analysis available today are laboratory methods, which result in major delays in response and numerous ways in which human involvement is required. The water samples must be taken, sent to the laboratory, then analyzed by different methods of analysis, some of which require special preparation of the sample. Among these methods are:
  potentiometric quantitative analysis for measuring sulfides,
  distillation, then calorimetric titration for ammonium hydroxide,
  high performance liquid phase chromatography for measuring phenols,
  UV oxidation, linear IR detection for Total Organic Carbon.

On the site of operations, at best it takes many minutes, even several hundred minutes after the samples are taken, until the refiner has results from the analysis, and then only with limited frequency, such as fewer than five times per 24-hour period of operation of the stripper.

The present invention therefore proposes to remedy the disadvantages of these different methods of laboratory analysis of the former technology by proposing a simultaneous analysis of the different pollutants usually present in industrial wastewater, using a single analysis method, ultraviolet spectrometry, directly and automatically applied to the feed water and/or output water of the stripper.

A purpose of the invention is also to have the results of the analyses nearly in real time, for continuous control of the stripper, using means already described in the technology, by controlling and regulating certain principal parameters of the stripper's operation, such as the feed flow rate of wastewater to be treated, and the flow rate of stripping water vapor.

To that end, a purpose of the present invention is a method for continuous processing of industrial wastewater that may contain various contaminants, according to which the wastewater is introduced by at least one feed line into a stripper column in which it flows by gravity, a flow of water vapor is injected into this column at a level such that the wastewater and the water vapor circulate in counter-current in the column, the gases extracted by this vapor stripping of the wastewater are recovered at the column head, and at the base of the stripper column the treated water is evacuated, this method being characterized in that:

- at least a portion of the ultraviolet spectrum of the compounds present in one or the other of the wastewater feed circuit or the outlet circuit of treated water from the column is determined on line;
- by mathematical processing of the measured intensities, at least one contaminant product present in the samples taken is determined qualitatively and quantitatively;
- depending on the results thus obtained, and by comparison to previously defined set points, this information is retrieved in the form of electrical signals that control the flow rates of the wastewater and water vapor feeds in the stripper column.

The taking of water samples, the measurements made in the domain of the ultraviolet light spectrum, the transmission of the electrical signals and the control of the operational units controlling the flow rates of wastewater and water vapor feeds are preferably performed by at least one programmed, automatic control device.

The analysis technique, which consists of:

1. using a commercial spectrometer to measure the UV spectrum from a sample, or a portion of this spectrum, or a specific wavelength thereof, whether the spectrum is emitted directly or by fluorescence, or absorbed by this sample, when the sample is excited by a source emitting ultraviolet light,
2. then applying to the intensities thus recorded, a mathematical processing, such as the deconvolution of spectra or PLS (partial least square), is well known to a person skilled in the art.

For example, reference can be made to the following two publications:

- O. Thomas, F. Theraulaz, C. Agnel, and S. Suryani ("Advanced UV examination of wastewater; Environmental Technology," 1996, vol. 17, pp 251-261);
- O. Thomas, F. Theraulaz, M. Domeizel, and C. Massiani ("UV spectral deconvolution: a valuable tool for wastewater quality determination," Environmental Technology 1993, vol. 14, pp 1187-1192).

This analysis technique that is known for its use in the laboratory and which consists of using UV spectrometry to measure the sulfides, ammonium hydroxide, or certain phenols in water, has required various adaptations in order to apply it to a continuous process directly on the circuits of the stripper.

Thus, for example, the presence of undissolved hydrocarbons in the process waters very quickly causes a fouling of the sampling line and of the measuring cell, disrupting the UV measurement. Consequently, to remedy this disadvantage, a coalescer should be installed at the head of the sample feed line, in order to keep only the aqueous phase of the sample for UV analysis.

Moreover, because the pH of process waters usually varies between 7 and 10, it is known that at pH 4 the sulfides in the form of $H_2S$ are not observable by UV spectrometry. In order to ensure an exhaustive analysis of these sulfides, the water sample must therefore be diluted with an aqueous buffer solution with a high pH, such as 10, so that regardless of the value of the pH of the sample to be analyzed, its dilution with the buffer solution will bring its pH back above 8, and preferably between 8 and 10, in which area all sulfides are observable and therefore measurable by UV spectrometry.

As a result of the continuous control mode of the stripper column used in this method, it is possible to more closely monitor the concentration(s) of the different contaminants contained in the water, for example at the outlet of the column, by automatically regulating the flow rates of wastewater feed or stripper water vapor. In addition, in the event of an abrupt increase in the concentration of one or more contaminants, a deviation of all or part of the flows of water to be treated upstream of the stripper can be implemented nearly in real time, automatically, to a temporary storage tank, for the possible application of a special treatment or to dilute said water.

The modification of the stripper's flow rates of feed water and vapor, as a function of the results of this analysis, is done in a conventional way known to a person skilled in the art.

In this regard, it will be noted that it is generally not possible to modify other operational parameters, such as the temperatures and pressures of the water flows entering or leaving the stripper. However, depending on the values measured by the ultraviolet spectrometer placed in line upstream or downstream from the stripper, the operator can automatically or non-automatically adjust the pH of the water for greater stripping effectiveness, while remaining within certain acceptable limits for the quality of the water disposed of in the natural environment.

The method, according to the invention, is applicable to any stripper associated with a refining unit (or any other industrial enterprise), in which waters are collected upstream from different units and/or secondary strippers that are associated therewith.

A purpose of the invention is also a device for continuous processing of wastewater of industrial origin, this device comprising:

- a stripper column for the water;
- at least a feed line of this stripper column for the water to be treated, this feed being at a level such that the water flows by gravity toward the bottom of the column;
- at least a feed line of the stripper column for water vapor intended to strip the gases contained in the water to be treated, the water vapor feed being at a level such that the wastewater and the water vapor circulate at countercurrents in the column;
- at the upper part of the column, at least a line for evacuating the water vapor and gases stripped from the wastewater by this vapor, with possibly a means for separating the gases and the vapor;
- at the lower part of the column, at least a line for evacuating the treated water;
- on the stripper column's wastewater and water vapor feed lines, controls for adjusting the flow rate, this device being characterized in that it comprises:
- on at least one wastewater feed line or on at least a treated water outlet line, a controlled means of taking a sample from the water circulating in this line;
- connected to these sample taking means, a means of analysis by ultraviolet spectrometry and an associated calculation means, for determining the presence and quantity of any contaminants present in the samples taken;
- connected to this calculation means, a programmed device for actuating the operational components to control the flow rate of the stripper column's wastewater feed lines and water vapor lines, as a function of the results of analysis of the samples.

As indicated above, this device can also advantageously include means for measuring other operational parameters, such as the temperature and pressure of the water flows entering and leaving the stripper column, and means of transmitting these measurements to the device for actuating the stripper column's operational control components.

Other characteristics and advantages of the invention, in its application to the treatment of wastewater from part of an oil refinery having an atmospheric distillation column and various associated facilities, will appear from the following detailed description. In this description, reference will be made to the appended drawings, in which.

Figure 1:
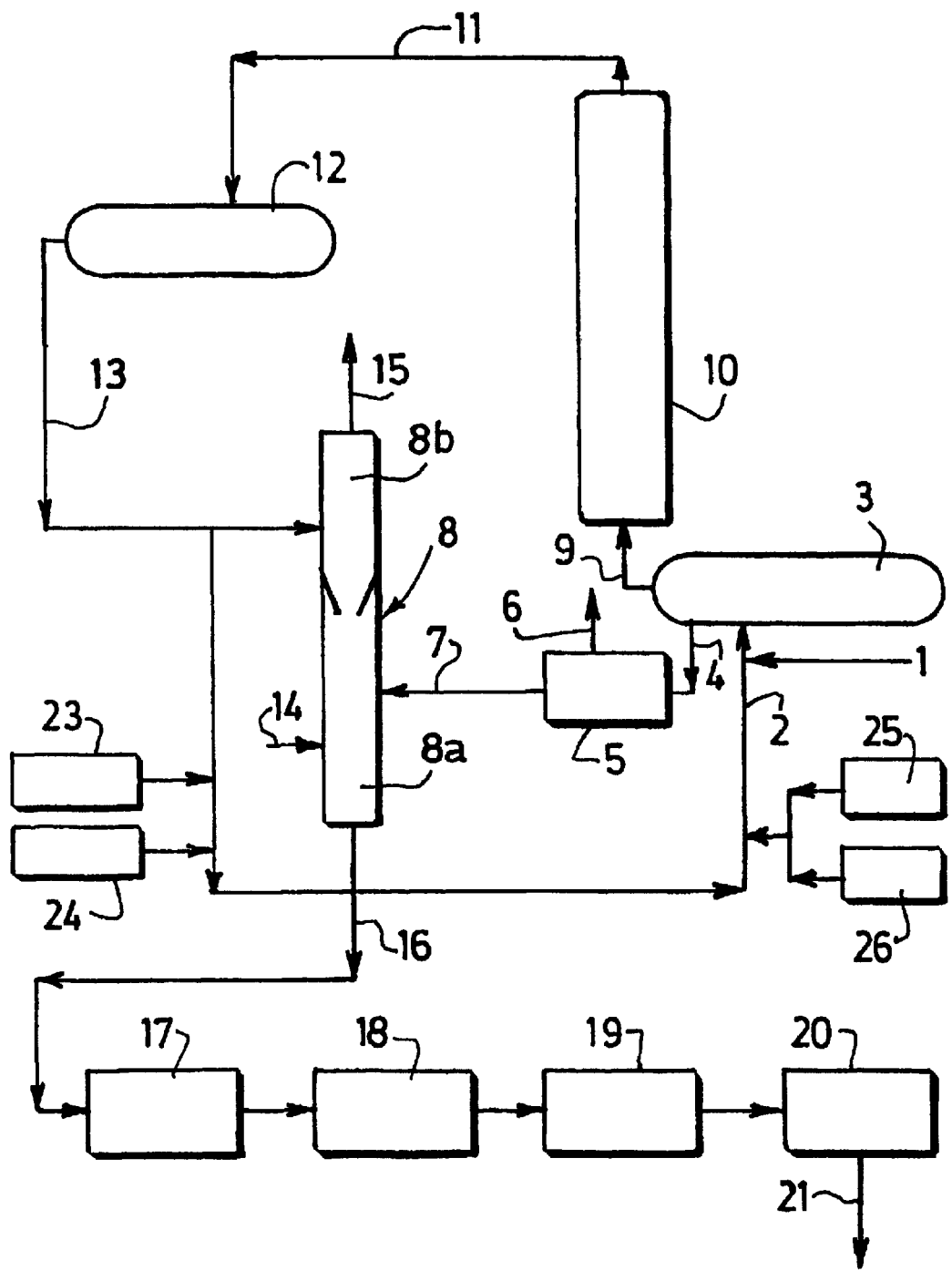
FIG. 1 is a partial diagrammatic view of the refinery's wastewater circuits, illustrating the position of the main water vapor column for stripping gases contained in the wastewater.

Reference will first be made to FIG. 1, in which, for purposes of simplification, only some of the primary strippers, preferably associated to each of the units, are shown in diagrammatic form.

The feed of crude oil and desalting water from the desalter 3 is provided respectively by lines 1 and 2. The salt water from the desalter 3 passes through the line 4 into a decanter where the liquid hydrocarbons present are evacuated by the line 6, while the salt water recovered by line 7 is injected into the lower part 8a of a stripper column 8, which, in this example, has two stages 8a and 8b.

The crude oil issuing from the desalter 3 is introduced by the line 9 into an atmospheric distillation column 10. The various outlet lines of the separate cross sections of said atmospheric distillation column 10 are not represented.

The vapors recovered at the column head are directed by the line 11 to a condensation recipient 12, where the condensed water is routed by the line 13 to the upper part 8b of the stripper column 8.

The water feed line 2 from the desalter is connected to the line 13 and various makeup feeds are introduced there, for example from a storage tank 23 of water from various origins, from a condensation tank 24 of effluents from a gas oil drying column head, and from various primary strippers associated with units of the facility, such as a stripper 25 from a gas oil desulfurization unit and a stripper 26 from a catalytic cracking unit.

In the column 8, the water introduced at 7 and at 13 trickle by gravity down toward the bottom, in counter-current to a water vapor flow introduced at a lower level by the line 14, and the gases dissolved in this water are stripped by the water vapor and evacuated at 15 with the remaining vapor at the upper part of the column 8. The water vapor can be generated by a continuous reboiling device located at the bottom of column 8.

The treated water is evacuated by line 16 at the lower part of the column 8 and it passes successively into a decanter 17, onto sand filters 18, into a bio-filter 19 and again into a clarification basin 20, before being evacuated by line 21 into the natural environment.

The bio-filter 19 is a runoff, systematic packing aerobic bacterial bio-filter, intended to ensure the destruction by micro-organisms of dissolved organic material, transforming it into biomass, carbonic acid gas and water. This bio-filter also provides for the nearly complete elimination of the hydrogen sulfide, primarily by aeration.

The bacteria of this bio-filter are very sensitive to certain pollutants, which are toxic to them above a certain concentration, equal for example to 8 mg/l for sulfides. It is important, therefore, to eliminate these contaminants or to reduce their concentration below thresholds upstream from the bio-filter, and in particular at the stripper.

As indicated above, one of the purposes of the present invention is specifically to control the operation of this stripper by continuously measuring the concentrations of various pollutants of the wastewater to be treated and/or pollutants of treated water, and by varying the stripper's feed flows of this water, of water vapor and possibly of recycled condensed water vapor, in order to operate under the most effective water purification conditions.

Figure 2:
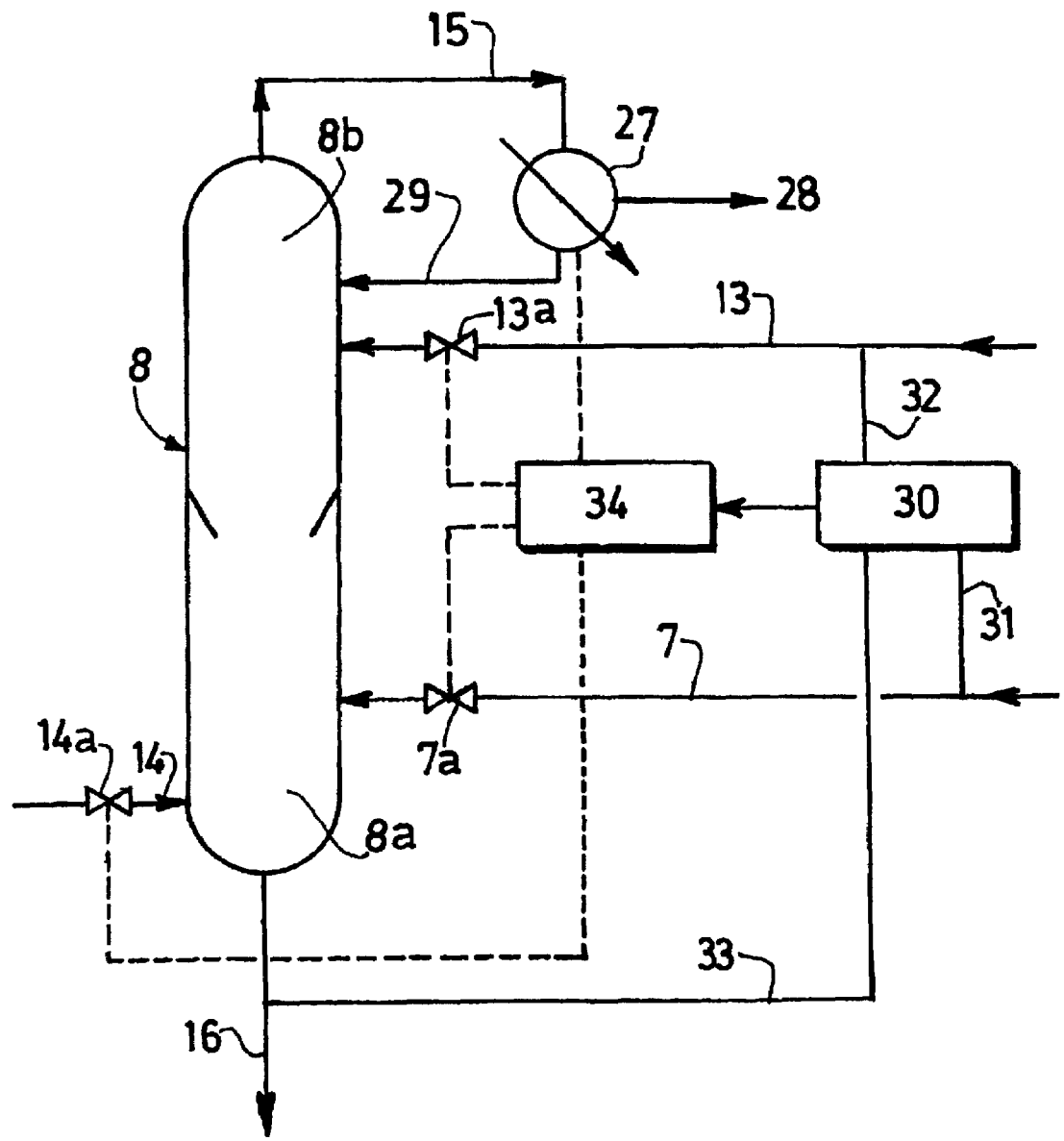
FIG. 2 is a partial diagrammatic view illustrating the control system according to the invention for the stripper column.

The following is in reference to FIG. 2.

FIG. 2 again shows the stripper column 8 of FIG. 1, the line 7 feeding water into this column water that issues from the crude oil desalter, the line 13 introducing other wastewater to be treated, line 14 injecting water vapor, line 15 evacuating, at the column head, the water vapor and the gases stripped by said vapor, and line 16 evacuating the treated water at the bottom of the column.

In this configuration, the line 15 feeds a condensation recipient 21, where the stripped gases are evacuated by the line 28, while the water produced by the condensation of the vapor is recycled by the line 29 at an adjustable reflux rate at the column head.

The lines 7, 13, and 14 have valves, respectively 7a, 13a and 14a, that allow the feed flow rate of the fluids circulating in the column 8 to be adjusted.

According to the invention, an ultraviolet spectrometry analyzer 30 is connected to the lines 7, 13, and 16, respectively, by the lines 31, 32, and 33, in order to take controlled samples of fluids circulating in these lines and to determine the concentration of certain contaminants present in said samples. Analyzers of this type are well known in the technology, and for example are marketed under the name IXO 510 by the SECOMAN company.

The spectra obtained are processed by spectral deconvolution in a programmed control center 34, that is, they are broken down into a certain number of spectra of the contaminants on which information is being sought (sulfides, chlorides, total organic carbon or TOC, materials in suspension or MIS, ammonium hydroxide, etc.). The spectra obtained are automatically compared to the spectra of a reference base composed of known samples, in order to determine the concentration of these contaminants in the samples. This method of analysis by deconvolution is described, for example, by S. Gallot and O. Thomas in "State of the art for the examination of UV spectra of waters and wastewaters," Intern. J. Environ. Anal. Chem., vol. 52, pp 119-158.

The control center 34 includes a control program which, depending on the analysis results, operates the valves 7a, 13a 14a and the condenser 27 to modify appropriately the feed flows of wastewater and water vapor in the column 8, as well as the rate of reflux of water at the column head.

The taking of samples can be controlled by an operator, or can be done automatically at regular intervals, such as every ten minutes, by the control center.

The great simplicity of implementation of the method according to the invention will be noted. The length of time required for the analyses is, generally around five minutes and the control of the stripper can consequently be carried out immediately after these analyses.

Although the invention has been described essentially in its application to processing wastewater of a refinery, it will be clear to a person skilled in the art that it also applies to the treatment of any other type of wastewater produced by different industrial facilities.

The invention claimed is:

1. Method for continuous processing of industrial wastewater that may contain various contaminants, according to which the wastewater is introduced by at least one feed line into a stripper column in which it flows by gravity, a flow of water vapor is injected into the column at a level such that the wastewater and the water vapor circulate in counter-current in the column, the gases extracted by the vapor stripping of the wastewater are recovered at the column head, and at the base of the stripper column the treated water is evacuated, the method comprising:

determining on line at least a portion of the ultraviolet spectrum of compounds present in one or the other of the at least one feed line or the treated water evacuated from the column, wherein the compounds are selected from the group consisting of sulfides, ammonium hydroxide, and phenols, and the determining on line is made on an aqueous portion of a sample, after separation from its organic phase;

mathematically processing measured intensities and thereby determining qualitatively and quantitatively at least one contaminant product present in the samples taken; and depending on results thus obtained, and by comparison to previously defined set points, retrieving information in the form of electrical signals that control the flow rates of the wastewater and water vapor feeds in the stripper column.

2. Method according to claim 1, wherein the taking of these water samples, their analysis by ultraviolet spectrometry and the transmission of the control signals for setting and adjusting the flow rates of wastewater and water vapor feeds of the stripper column are controlled by at least a programmed, automatic control device.

3. Method according to claim1, wherein the sample is diluted, prior to being measured by UV spectrometry, in a buffer aqueous solution, to bring its pH to a value higher than 8.

4. Method according to any one of claims 1 to 2 and 3, wherein the pH of the water to be treated is adjusted in accordance with the results of the UV spectrometry measurements.

5. Method according to any one of claims 1 to 2 and 3, wherein the wastewater to be treated is introduced into the stripper column at at least two different levels thereof.

6. Method according to any one of claims 1 to 2 and 3, wherein the gases extracted by stripping from the wastewater are separated from the water vapor in a condensation recipient and evacuated for possible subsequent treatment.

7. Method according to claim 6, wherein the water produced by the condensation of the vapor in the condensation recipient is recycled at the column head with an adjustable rate of reflux.

8. Method according to any one of claims 1 to 2 and 3, wherein the vapor introduced at the base of the column is generated by a continuous reboiling device located at the bottom of the column.

9. Method according to any one of claims 1 to 2 and 3, wherein the wastewater to be treated is introduced into the lower part of the stripper column and in the upper part thereof.

10. Device for continuous processing of wastewater of industrial origin, the device comprising:

a stripper column for the water to be treated;

at least one feed line of the stripper column for the water to be treated, the at least one feed line of the water to be treated being at a level such that the water flows by gravity toward the bottom of the column;

at least one feed line of the stripper column for water vapor intended to strip gases contained in the water to be treated, the at least one feed line of the water vapor being at a level such that the wastewater and the water vapor circulate at counter-currents in the column;

at an upper part of the column, at least a line for evacuating the water vapor and gases stripped from the wastewater by the water vapor, with optionally a means for separating the gases and the water vapor;

at a lower part of the column, at least a line for evacuating the treated water; and on the stripper column's wastewater and water vapor feed lines, controls for adjusting the flow rate;

the device comprising:

on at least a wastewater feed line or on at least the treated water outlet line, a controlled means of taking a sample from the water circulating in the line;

a coalescer installed at a head of the sample taking means;

connected to the sample taking means, a means of analysis by ultraviolet spectrometry and an associated calculation means, for determining the presence and quantity of contaminants selected from the group consisting of sulfides, ammonium hydroxide, and phenols present in the samples taken; and connected to the calculation means, a programmed device for actuating operational components to control the flow rate of the stripper column's wastewater feed lines and water vapor lines, as a function of the results of analysis of the samples.

11. Device according to claim 10, further comprising a means of programmed control of the means of taking samples of the wastewater and the treated water.

12. Device according to either of claim 10 or 11, wherein the stripper column has two different stages each receiving a portion of the water to be treated.

13. Device according to either of claim 10 or 11, further comprising a condensation recipient located at the head of the column, in order to separate the stripped gases and the water vapor.

14. Device according to claim 13, wherein the reflux rate at the column head of the condensation water from the water vapor is adjustable.

15. Device according to either of claim 10 or 11, further comprising a reboiler located at the bottom of the column, in order to transform the condensation water into water vapor.

16. Method according to claim 1, wherein the wastewater is from an oil refinery.

17. Method according to claim 3, wherein the sample is diluted, prior to being measured by UV spectrometry, in a buffer aqueous solution, to bring its pH to a value between 8 and 10.

18. Device according to claim 10, wherein the device is for treating wastewater from an oil refinery.

* * * * *